(12) United States Patent
Yuthavong et al.

(10) Patent No.: US 7,371,758 B2
(45) Date of Patent: May 13, 2008

(54) ANTIMALARIAL PYRIMIDINE DERIVATIVES AND METHODS OF MAKING AND USING THEM

(75) Inventors: Yongyuth Yuthavong, Bangkok (TH); Bongkoch Tarnchompoo, Bangkok (TH); Sumalee Kamchonwongpaisan, Bangkok (TH)

(73) Assignee: National Science & Technology Development Agency (TH)

( * ) Notice: Subject to any disclaimer, the term of this patent is extended or adjusted under 35 U.S.C. 154(b) by 352 days.

(21) Appl. No.: 10/386,613

(22) Filed: Mar. 13, 2003

(65) Prior Publication Data

US 2004/0180913 A1      Sep. 16, 2004

(51) Int. Cl.
    *A01N 43/54*      (2006.01)
(52) U.S. Cl. .................. 514/272; 544/325; 514/272
(58) Field of Classification Search ................ 424/9.1, 424/9.2; 544/224, 242, 298, 311, 322, 323; 514/272
    See application file for complete search history.

(56) References Cited

U.S. PATENT DOCUMENTS

| | | | |
|---|---|---|---|
| 2,576,939 A | 12/1951 | Hitchings et al. | |
| 2,594,309 A | 4/1952 | Hitchings et al. | |
| 2,602,794 A | 7/1952 | Hitchings et al. | |
| 2,624,731 A | 1/1953 | Hitchings et al. | |
| 2,680,740 A | 6/1954 | Jacob | |
| 2,688,019 A | 8/1954 | Hitchings et al. | |
| 3,849,416 A | 11/1974 | Mentha et al. | |
| 3,939,181 A | 2/1976 | Mentha et al. | |
| 3,940,393 A | 2/1976 | Greenspan et al. | |
| 4,992,444 A | 2/1991 | Stevens et al. | |

FOREIGN PATENT DOCUMENTS

GB           2158068 A    * 11/1985

OTHER PUBLICATIONS

Oppenlander et al., "Photooxygenation of 5-Aryl-2,4-diaminopyrimidines leading to 4-Amnio-1,3,5-triazin-2-yl Ketones and, in the Presence of Sodium Borohydride, to 5,6,-dihydro-4(3H)-pyrimidinones", Helvetica Chimica Acta, vol. 71 1998), pp. 712-717.*
Tarnchompoo et al., "Development of 2,4-diaminopyrimidines as antimalarials . . . ", J. Med. Chem., 2002, 45, 1244-1252.*
Baker et al., "Irreversible Enzyme Inhibitors . . . " J. Med. Chem., 1970, 13 (6), 1143-1148.*
Tarnchompoo et al., "Development of 2,5-Diaminopyrimidines . . . " J.Med.Chem. 2002, 45, 1244-1252.*
Nicholas J. White, "Antimalarial Drug Resistance", *The Journal of Clinical Investigation* (Apr. 2004), pp. 1084-1092, vol. 113, No. 8, Review Series; Faculty of Tropical Medicine, Mahidol University, Bangkok, Thailand; Centre for Vaccinology and Tropical Medicine, Churchill Hospital, Oxford, United Kingdom.

Alsia P. Alker et al., "Mutations Associated with Sulfadoxine-Pyrimethamine and Chlorproguanil Resistance in *Plasmodium falciparum* Isolates from Blantyre, Malawi", *Antimicrobial Agents and Chemotherapy* (Sep. 2005), pp. 3919-3921, vol. 49, No. 9; American Society for Microbiology.
Alexis Nzila et al., "Why has the dihydrofolate reductase 164 mutation not consistently been found in Africa yet?", *Transactions of the Royal Society of Tropical Medicine and Hygiene* (2005), pp. 341-346, vol. 99; Elsevier.
Russell, P.B. et al. (1951). "2,4-Diaminopyrimidines as Antimalarials. III. 5-Aryl Derivatives," J. Am. Chem. Soc. 73:3763-3770.
Trager, W. et al., (1976). "Human Malaria Parasites in Continous Culture," Science, 193:673-675.
Desjardins, R.E. et al. (1979). "Quantitative Assessment of Antimalarial Activity in Vitro by a Semiautomated Microdilution Technique," Antimicrob. Agents Chemother. 16(6):710-718.
Blaney, J.M. et al. (1984). "Structure-Activity Relationships of Dihydrofolate Reductase Inhibitors," Chem. Rev. 84:333-407.
Cowman, A.F et al. (Dec. 1988). "Amino acid changes linked to pyrimethamine resistance in the dihydrofolate reductase-thymidylate synthase gene of Plasmodium falciparum," Proc. Natl. Acad. Sci. USA, 85: 9109-9113.
Peterson, D.S. et al. (Dec. 1988). "Evidence that a point mutation in dihydrofolate reductase-thymidylate synthase confers resistance to pyrimethamine in falciparum malaria," Proc. Natl. Acad. Sci. USA, 85: 9114-9118.
Peterson, D.S. et al. (Apr. 1990). "Molecular basis of differential resistance to cycloguanil and pyrimethamine in Plasmodium falciparum malaria," Proc. Natl. Acad. Sci. USA, 87:3018-3022.
Skehan, P. et al. (1990). "New Colorimetric Cytotoxicity Assay for Anticancer-Drug Screening," J. Natl. Cancer Inst. 82(13):1107-1112.
Barlin, G.B. et al. (1996). "Potential Antimalarials. XXII. Some 2,4-Biamino-5-(3-and 4-trifluoromethylphenyl and 3,4-methylenedioxyphenyl) pyrimidines," Aust. J. Chem. 49: 647-650.
McKie, J. H. et al. (1998). "Rational Drug Design Approach for Overcoming Drug Resistance: Application to Pyrimethamine Resistance in Malaria," J. Med. Chem. 41:1367-1370.
Ahmed, A. et al. (2004). "Plasmodium falciparum Isolates in India Exhibit a Progressive Increase in Mutations Associated with Sulfadoxine-Pyrimethamine Resistance," Antimicrobial Agents and Chemotherapy, 48(3):879-889.
Gregson et al. (2005). "Mechanisms of Resistance of Malaria Parasites to Antifolates," Pharmacological Reviews, 57(1):117-145.

* cited by examiner

*Primary Examiner*—Mark Berch
*Assistant Examiner*—Paul V. Ward
(74) *Attorney, Agent, or Firm*—Morrison & Foerster LLP

(57) ABSTRACT

Compounds of the formula (I) wherein $R^1$ represents a hydrogen atom or a 3-halogen atom, and $R^2$ represents a straight-chain alkyl group containing up to 6 carbon atoms, a straight-chain alkyl group containing up to 3 carbon atoms with unsubstituted or substituted aromatic ring, or alkoxycarbonyl substituent at the end position, or aryloxyalkoxyalkyl group have been found to possess antimalarial activity against *Plasmodium falciparum* lines, including those resistant against pyrimethamine and other antifolates. The compounds themselves, methods of making these compounds, and methods of using these compounds are all disclosed.

14 Claims, 1 Drawing Sheet

ANTIMALARIAL PYRIMIDINE DERIVATIVES AND METHODS OF MAKING AND USING THEM

CROSS-REFERENCE TO RELATED APPLICATION

Not Applicable

STATEMENT REGARDING FEDERALLY SPONSORED RESEARCH OR DEVELOPMENT

Not Applicable

REFERENCE TO SEQUENCE LISTING

Not Applicable

BACKGROUND OF THE INVENTION

The 2,4-diaminopyrimidine derivative compounds have been extensively studied as inhibitors of dihydrofolate reductase (DHFR). In the living cell, DHFR reduces dihydrofolate to tetrahydrofolate, which is further used to produce 5,10-methylenetetrahydrofolate, a substance essential for DNA synthesis and cell growth. Inhibition of DHFR results in inhibition of DNA synthesis, and in cell death. Many DHFR inhibitors, also known as antifolates, are therefore potentially useful drugs against infectious agents, provided that they can specifically inhibit DHFR of the target cells without substantially affecting the cells of the host.

Many 2,4-diaminopyrimidine derivative compounds have been synthesized and shown to have antimalarial activities. These compounds include pyrimethamine (Pyr) and derivatives thereof, with substituents on the 5-phenyl group, and substituents on position 6. The synthetic processes generally involve three steps: a) preparation of keto nitrile via an acylation of the arylacetonitrile with ester as catalyzed by an alkali alkoxide, b) preparation of the corresponding β-alkoxyacrylonitrile or the corresponding ketal of the keto nitrile, c) preparation of 2,4-diaminopyrimidine by treatment of the above intermediate with guanidine in alcoholic solution. Due to low yield of keto nitrile together with decomposed/polymerized compounds of the previous methods, the present invention provides a modified method, employing effective acylating reagents, base, reaction conditions and solvents in three steps, for the preparation of pyrimethamine derivative compounds in better overall yields.

Although pyrimethamine and other described 2,4-diaminopyrimidine derivative compounds are effective against wild type malaria parasites, they are not effective against resistant parasites, which have been shown to bear mutations in the dihydrofolate reductase, for examples, mutations of *Plasmodium falciparum* dihydrofolate reductase at positions 108 (serine to asparagine), 51 (asparagine to isoleucine), 59 (cysteine to arginine) and 164 (isoleucine to leucine). The degree of resistance generally increases with the number of mutations the parasite accumulates, prompting the need for novel drugs which are effective both against sensitive and resistant strains of malaria parasites. These drugs must, moreover, be of low toxicity to the human host. It is also preferable that these drugs do not have significant antibacterial activity, since they often have to be administered over extended periods. Under such circumstances, there would be a danger of development of resistant strains of bacteria if the drugs also have significant antibacterial activity.

The present invention describes compounds which are effective against malaria, in particular drug-resistant malaria arising from mutations as described. A number of these compounds have low toxicity to the human host and are therefore useful in suitable pharmaceutical compositions. They have little antibacterial activities and are unlikely to lead to development of resistant strains of bacteria on deployment. The procedure for their synthesis is also described.

BRIEF SUMMARY OF THE INVENTION

This invention meets the need for more effective compounds against malaria, in particular drug-resistant malaria specifically arising from resistance to inhibition of the parasite dihydrofolate reductase by antifolate drugs. This invention provides compounds of formula (I) wherein $R^1$ represents a hydrogen atom or a 3-halogen atom, and $R^2$ represents a straight-chain alkyl group containing up to 6 carbon atoms, a straight-chain alkyl group containing up to 3 carbon atoms with unsubstituted or substituted aromatic ring, or alkoxycarbonyl substituent at the end position, or aryloxyalkoxyalkyl group.

Methods for synthesis of the above compounds are also disclosed which comprise three steps: a) acylation of arylacetonitrile (II) with acid chloride (III) employing lithium diisopropylamide in tetrahydrofuran at −78° C. affords the desired keto nitrile (IV); b) reaction of keto nitrile (IV) with diazomethane in dioxane at room temperature affords the corresponding β-methoxyacrylonitrile (V); c) condensation reaction of the β-methoxyacrylonitrile (V) with guanidine in dimethyl sulfoxide at 80° C. provides the desired pyrimethamine derivative compound (I).

This invention provides methods for therapeutically and/or prophylactically using the compounds described, and pharmaceutically acceptable salts and products thereof.

It is an object of this invention to provide 2,4-diaminopyrimidine derivative compounds, and pharmaceutically acceptable salts thereof, for substantially inhibiting dihydrofolate reductase enzymes.

It is an object of this invention to provide 2,4-diaminopyrimidine derivative compounds, and pharmaceutically acceptable salts thereof, having antimalarial activity, including activity against drug-resistant malaria both by themselves and in synergistic combinations with sulfonamides and/or other agents.

It is an object of this invention to provide methods for synthesizing 2,4-diaminopyrimidine derivative compounds, and pharmaceutically acceptable salts thereof.

DETAILED DESCRIPTION OF THE INVENTION

1. Preparation of 2,4-Diaminopyrimidine Derivative Compounds

Figure 1:
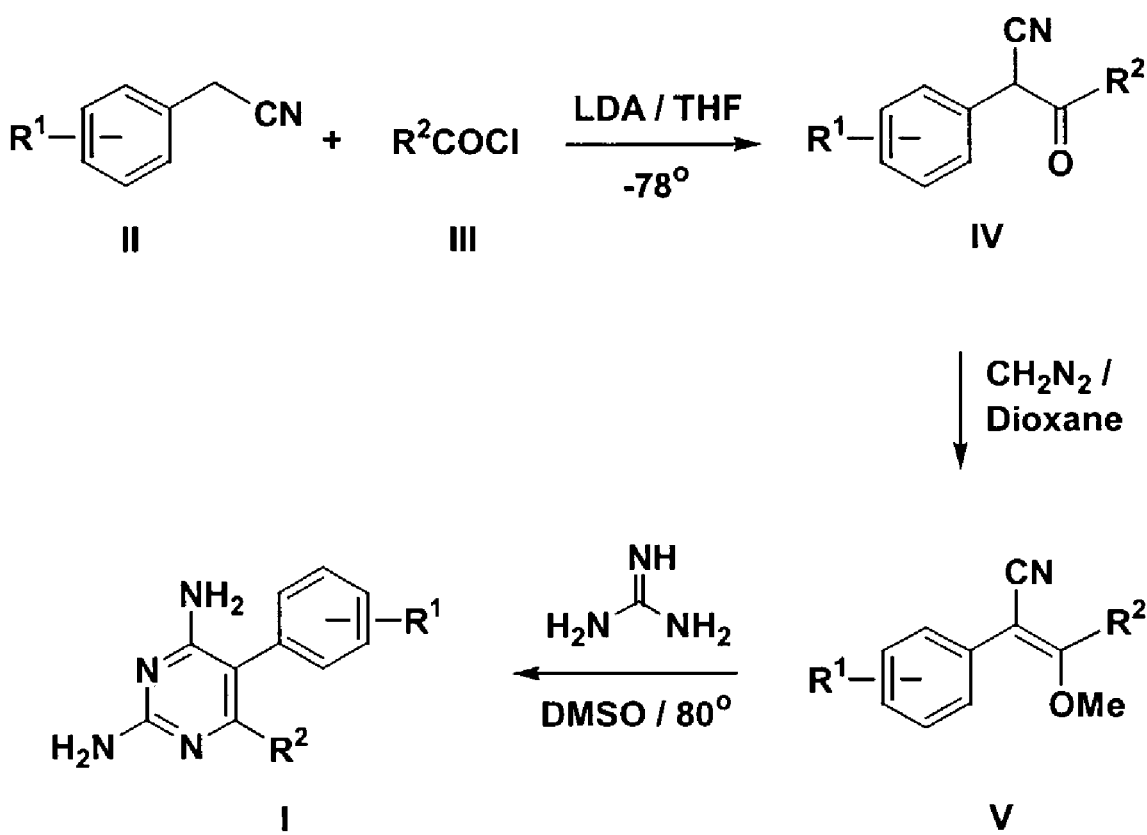
FIG. 1 shows a schematic diagram of preparation method of 2,4-diaminopyrimidine derivative compounds of formula I.

In the present invention, a modified method shown in FIG. 1 has been employed for the preparation of 2,4- diaminopyrimidine derivative compounds of the general formula (I), wherein $R^1$ represents a hydrogen atom or a 3-halogen atom, and $R^2$ represents a straight-chain alkyl group containing up to 6 carbon atoms, a straight-chain alkyl group containing up to 3 carbon atoms with unsubstituted or substituted aromatic ring, or alkoxycarbonyl substituent at the end position, or aryloxyalkoxyalkyl group.

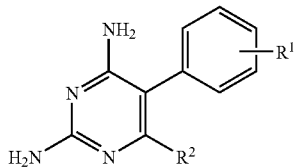

The modified method said above is described in detail below.

1.1 Preparation of Keto Nitrile (III)

To a solution of lithium diisopropylamide (20 mmol, 1 equivalent) in tetrahydrofuran (30 mL) at −78° C. was added slowly a solution of arylacetonitrile (II) (20 mmol, 1 equivalent) in tetrahydrofuran (30 mL) and the reaction mixture was left stirring at −78° C. for 1 hour. A solution of acid chloride (III) (20 mmol, 1 equivalent) in tetrahydrofuran (5 mL) was added into the reaction at −78° C. After quenching with saturated aqueous ammonium chloride solution, the crude mixture was extracted three times with dichloromethane. The combined dichloromethane extracts were successively washed with water, saturated aqueous sodium chloride solution, dried over magnesium sulfate, filtered, and evaporated to dryness under reduced pressure. Purification of the crude product by column chromatography gave the desired keto nitrile (IV).

1.2 Preparation of β-Methoxyacrylonitrile (V)

Diazomethane gas, generated from a reaction of diazald and sodium hydroxide solution, was passed into a solution of keto nitrile (IV) (5 mmol) in cold dioxane (10 mL). The reaction mixture was left at room temperature overnight and evaporated to dryness under reduced pressure to give the corresponding β-methoxyacrylonitrile (V) in quantitative yield. The crude product was further used in the next step without purification.

1.3 Condensation Reaction of the β-Methoxyacrylonitrile (V) with Guanidine

A mixture of β-methoxyacrylonitrile (IV) (3 mmol) and guanidine (5 mmol) in dimethyl sulfoxide (5 mL) was heated at 80° C. for 5 min under $N_2$. The reaction mixture was poured into cold water. The precipitate obtained was collected by filtration and washed successively with water. Recrystallization from ethanol gave white crystals of 2,4-diaminopyrimidine derivative compounds (I).

As the result of the said procedure above, the invented compounds have been generated and some are listed below.

EXAMPLE 1

2,4-diamino-6-(n-hexyl)-5-phenylpyrimidine white crystals, mp 155-156° C., $^1$H (400 MHz, DMSO-$d_6$) δ 0.77 (t, J=7.5Hz, 3H), 1.03-1.17 (m, 6H), 1.38-1.44 (m, 2H), 2.08-2.11 (m, 2H), 5.47 (s, 2H, $NH_2$), 5.85 (s, 2H, $NH_2$), 7.17 (d, J=7.3Hz, 2H), 7.34 (dd, J=7.3,7.4Hz, 1H), 7.43 (dd, J=7.4, 7.5Hz, 2H); $^{13}$C (100 MHz, DMSO-$d_6$) δ 14.72, 22.71, 28.95, 29.33, 31.67, 34.88, 107.88, 127.97, 129.71, 131.46, 136.82, 162.74, 162.85, 166.31; MS (ESITOF) m/z: Calcd. for $C_{16}H_{22}N_4$: 270.38; found: 271.4. Anal. C, 71.08; H, 8.20; N, 20.72. Found: C, 71.11; H, 8.24; N, 20.77.

EXAMPLE 2

2,4-diamino-5-phenyl-6-(3-phenylpropyl)pyrimidine white crystals, mp 154-154.5° C. $^1$H (400 MHz, DMSO-$d_6$) δ 1.74 (m, 2H), 2.13 (m, 2H), 2.13 (m, 2H), 2.41 (dd, J=7.6, 7.6Hz, 2H), 5.45 (s, 2H, $NH_2$), 5.87 (s, 2H, $NH_2$), 7.03 (d, J=7.3Hz, 2H), 7.11-7.23 (m, 5H), 7.33-7.36 (m, 1H), 7.40-7.44 (m, 2H); $^{13}$C (100 MHz, DSMO-$d_6$) δ 30.65, 34.61, 35.80, 107.93, 126.42, 127.95, 128.99, 129.75, 131.43, 136.74, 142.64, 162.79, 162.87, 165.88; MS (ESITOF) m/z: Calcd. for $C_{19}H_{20}N_4$: 304.40; found: 305.20. Anal. C, 74.97; H, 6.62; N, 18.41. Found: C, 74.85; H, 6.52; N, 18.46.

EXAMPLE 3

2,4-diamino-6-(3-methoxycarbonylpropyl)-5-phenylpyrimidine white crystals, mp 174-175° C. $^1$H (400 MHz, DMSO-$d_6$) δ 1.77 (m, 2H), 2.10-2.18 (m, 4H), 3.49 (s, 3H), 6.06 (s, 2H, $NH_2$), 6.15 (s, 2H, $NH_2$), 7.16 (m, 2H), 7.33-7.37 (m, 1H), 7.42-7.46 (m, 2H); $^{13}$C (100 MHz, DMSO-$d_6$) δ 24.18, 33.80, 33.93, 51.96, 108.05, 127.98, 129.76, 131.43, 136.67, 162.80, 162.90, 165.20, 173.80; MS (ESITOF) m/z: Calcd. for $C_{15}H_{18}N_4O_2$: 286.34; found: 287.18. Anal. C, 62.92; H, 6.34; N, 19.57. Found: C, 62.64; H, 6.39; N, 19.89.

EXAMPLE 4

2,4-diamino-5-(3-chlorophenyl)-6-(3-phenylpropyl)pyrimidine white crystals, mp 140-141° C. $^1$H (400 MHz, DMSO-$d_6$) δ 1.75 (m, 2H), 2.10 (m, 2H), 2.43 (dd, J=7.4, 7.4Hz, 2H), 5.65 (s, 2H, $NH_2$), 5.93 (s, 2H, $NH_2$), 7.03 (d, J=7.3Hz, 2H), 7.10-7.14 (m, 2H), 7.19-7.22 (m, 3H), 7.38-7.44 (m, 2H); $^{13}$C (100 MHz, DSMO-$d_6$) δ 30.50, 34.52, 35.71, 106.68, 126.44, 127.97, 128.98, 130.37, 131.26, 131.46, 134.14, 139.13, 142.54, 162.74, 162.96, 165.98; MS (ESITOF) m/z: Calcd. for $C_{19}H_{19}ClN_4$: 338.84; found: 339.18. Anal. C, 67.35; H, 5.65; N, 16.53. Found: C, 67.34; H, 5.47; N, 16.50.

EXAMPLE 5

2,4-diamino-5-(3-chlorophenyl)-6-[3-(4-methoxyphenyl)propyl]pyrimidine white crystals, mp 111-111.5° C. $^1$H (400 MHz, DMSO-$d_6$) δ 1.68 (m, 2H), 2.06 (dd, J=7.7, 7.7Hz, 2H), 2.34 (dd, J=7.4, 7.4Hz, 2H), 3.68 (s, 3H), 5.57 (s, 2H, $NH_2$), 5.86 (s, 2H, $NH_2$), 6.74 and 6.91 (AB quartet, J=8.5Hz, 4H), 7.08 (m, 1H), 7.16 (m,1H), 7.36-7.42 (m, 2H), $^{13}$C (100 MHz, DMSO-$d_6$) δ 30.75, 34.44, 34.78, 55.77, 106.67, 114.39, 127.96, 129.87, 130.36, 131.24, 131.47, 134.14, 134.34, 139.09, 158.11, 162.74, 162.94, 166.13; MS (ESITOF) m/z: Calcd. for $C_{20}H_{21}ClN_4O$: 368.87; found: 369.21. Anal. C, 65.12; H, 5.74; N, 15.19. Found: C, 65.22; H, 5.66; N, 15.24.

EXAMPLE 6

2,4-diamino-5-(3-chlorophenyl)-6-(3-methoxycarbonylpropyl)pyrimidine white crystals, mp 187.5-188° C. $^1$H (400 MHz, DMSO-$d_6$) δ 1.71 (m, 2H), 2.09 (dd, J=7.5, 7.5Hz, 2H), 2.16 (dd, J=7.3, 7.3Hz, 2H), 3.48 (s, 3H), 5.60 (s, 2H, $NH_2$), 5.90 (s, 2H, $NH_2$), 7.10 (m, 1H), 7.18 (m, 1H), 7.37-7.45 (m, 2H); $^{13}$C (100 MHz, DMSO-$d_6$) δ 24.05, 33.72, 33.88, 51.97, 106.82, 128.00, 130.40, 131.26, 131.50, 134.15, 139.07, 162.75, 162.98, 165.26, 173.86; MS (ESITOF) m/z: Calcd. for $C_{15}H_{17}ClN_4O_2$: 320.78, found: 321.13. Anal. C, 56.17; H, 5.34; N, 17.47. Found: C, 56.18; H, 5.35; N, 17.45.

EXAMPLE 7

2,4-diamino-5-(3-chlorophenyl)-6-[2-(3-phenoxypropyloxy)ethyl]pyrimidine white crystals, mp 93-94° C. $^1$H (400 MHz, DMSO-$d_6$) δ 1.86 (m, 2H), 2.34 (m, 2H), 3.39 (dd, J=6.3, 6.3Hz, 2H), 3.56 (m, 2H), 3.93 (dd, J=6.3, 6.3Hz, 2H), 5.67 (s, 2H, $NH_2$), 5.91 (s, 2H, $NH_2$), 6.87-6.93 (m, 3H), 7.16 (d, J=7.0Hz, 1H), 7.25-7.29 (m, 3H), 7.37-7.45 (m, 2H), $^{13}$C (100 MHz, DMSO-$d_6$) δ 29.90, 35.29, 65.21, 67.39, 69.77, 107.46, 115.25, 121.30, 128.02, 130.33, 130.42, 131.41, 131.48, 134.10, 138.93, 159.38, 162.77, 162.87, 163.35; MS (ESITOF) m/z: Calcd. for $C_{21}H_{23}ClN_4O_2$: 398.89; found: 399.40. Anal. C, 63.23; H, 5.81; N, 14.05. Found: C, 63.15; H, 5.81; N, 14.04.

2. Enzyme Inhibitory, Antimalarial and Other Properties of the Invented Compounds

2.1 Determination of Enzyme Inhibition Constants ($K_i$)

It is an object of this invention to provide 2,4-diaminopyrimidine derivative compounds, and pharmaceutically acceptable salts thereof, for substantially inhibiting dihydrofolate reductase enzymes. Enzymes, comprising dihydrofolate reductase of *Plasmodium falciparum*, wild type, single (S108N), double (C59R+S108N), triple (N51+C59R+S108N, C59R+S108N+I164L), and quadruple (N51+C59R+S108N+I164L) mutants, were prepared from *E. coli* expression system (*E. coli* BL21 (DE3)pLysS) containing the corresponding genes. The activity of the enzymes was determined spectrophotometrically at 25° C. The reaction (1 mL) contained 1×DHFR buffer (50 mM TES, pH 7.0, 75 mM β-mercaptoethanol, 1 mg/mL Bovine Serum Albumin), 100 μM each of the substrate dihydrofolate and cofactor NADPH, and appropriate amount of affinity-purified enzyme to initiate the reaction (0.001-0.005 units in phosphate buffer containing 50 mM KCl).

The inhibition of the enzymes with the invented compounds was investigated in a 96 well plate with 200 μL of the above mixture in the presence of antifolate. The kinetics was followed at 340 nm. The $K_i$ values of the inhibitors for the wild type and mutant enzymes were determined by fitting to the equation $IC_{50}=K_i (1+([S]/K_m))$, where $IC_{50}$ is the concentration of inhibitor which inhibits 50% of the enzyme activity under the standard assay condition and $K_m$ is the Michaelis constant for the substrate dihydrofolate.

The inhibition constants ($K_i$) of the invented compounds against wild type and mutants PfDHFR are as summarized in Table 1.

TABLE 1

Inhibition constants ($K_i$) of 2,4-diaminopyrimidine derivative compounds for binding with wild type and mutant PfDHFRs

| | $K_i$ (nM) | | | | | |
|---|---|---|---|---|---|---|
| Example | Wild type | S108N | C59R + S108N | N51I + C59R + S108N | C59R + S108N + I164L | N51I + C59R + S108N + I164L |
| Pyr | 0.6 ± 0.2 | 28.6 ± 2.3 | 53.9 ± 6.5 | 67.1 ± 4.2 | 112 ± 17 | 385 ± 163 |
| 1 | 0.3 ± 0.1 | 1.2 ± 0.3 | 0.7 ± 0.3 | 0.4 ± 0.02 | 0.7 ± 0.2 | 1.4 ± 0.5 |
| 2 | 0.5 ± 0.0 | 0.9 ± 0.2 | 2.4 ± 0.1 | 1.1 ± 0.1 | 1.9 ± 0.1 | 4.7 ± 0.9 |
| 3 | 0.6 ± 0.0 | 1.8 ± 0.2 | 5.5 ± 0.5 | 3.3 ± 0.6 | 15 ± 3 | 24 ± 2 |
| 4 | 1.2 ± 0.2 | 3.0 ± 0.6 | 4.2 ± 0.2 | 2.0 ± 0.2 | 2.2 ± 0.3 | 2.0 ± 0.8 |
| 5 | 2.2 ± 0.6 | 4.0 ± 0.2 | 6.0 ± 0.6 | 1.3 ± 0.1 | 2.9 ± 0.3 | 2.0 ± 0.4 |
| 6 | 0.5 ± 0.0 | 1.7 ± 0.1 | 2.8 ± 0.2 | 0.8 ± 0.2 | 1.8 ± 0.4 | 2.7 ± 1.2 |
| 7 | 0.4 ± 0.2 | 1.8 ± 0.3 | 1.9 ± 0.4 | 0.7 ± 0.1 | 1.3 ± 0.4 | 1.7 ± 0.2 |

2.2 Determination of Antimalarial Activities ($IC_{50}$)

It is an object of this invention to provide 2,4-diaminopyrimidine derivative compounds, and pharmaceutically acceptable salts thereof, having antimalarial activity, including activity against drug-resistant malaria both by themselves and in synergistic combinations with sulfonamides and/or other agents. *P. falciparum* strains were used in this study. *P. falciparum* strains were maintained continuously in human erythrocytes at 37° C. under 3% $CO_2$ in RPMI 1640 culture media supplemented with 25 mM HEPES, pH 7.4, 0.2% $NaHCO_3$, 40 μg/mL gentamicin and 10% human serum.

In vitro antimalarial activity was determined by using [$^3$H]-hypoxanthine incorporation method. The drugs were initially dissolved in DMSO and diluted with the culture media. Aliquots (25 μL) of the drug of different concentrations were dispensed in 96-well plates and 200 μL of 1.5% cell suspension of parasitized erythrocytes containing 1-2% parasitemia were added. The final concentration of DMSO (0.1%) did not affect the parasite growth. The mixtures were incubated in a 3% $CO_2$ incubator at 37° C. After 24 h of incubation, 25 μL (0.25 μCi) of [$^3$H]-hypoxanthine were added to each well. The parasite cultures were further incubated under the same condition for 18-24 h. DNA of parasites was harvested onto glass filter paper. The filters were air-dried and 20 μL liquid scintillation fluid was added. The radioactivity on the filters was then measured using a microplate scintillation counter. The concentration of inhibitor which inhibited 50% of the parasite growth ($IC_{50}$) was determined from the sigmoidal curve obtained by plotting the percentages of [$^3$H]-hypoxanthine incorporation against drug concentrations. Examples of the invented compounds in this series with active antimalarial activity against wild type and in particular against parasites carrying single, double, triple, and quadruple mutant enzymes are as summarized in Table 2.

TABLE 2

Anti-plasmodial activities ($IC_{50}$) of 2,4-diaminopyrimidine derivative compounds against *Plasmodium falciparum* with wild type (TM4/8.2) and the mutant enzymes: K1CB1 (C59R + S108N), W2 (N51I + C59R + S108N), Csl-2 (C59R + S108N + I164L), and V1/S (N51I + C59R + S108N + I164L)

| Example | $IC_{50}$ (µM) | | | | |
|---|---|---|---|---|---|
| | TM4/8.2 | K1CB1 | W2 | Csl-2 | V1/S |
| Pyr | 0.08 ± 0.01 | 30.9 ± 8.4 | 73.1 ± 7.4 | 41.7 ± 14.8 | >100 |
| 1 | 0.06 ± 0.02 | 1.3 ± 0.1 | 2.3 ± 0.7 | 3.0 ± 1.1 | 6.4 ± 2.9 |
| 2 | 0.21 ± 0.06 | 2.3 ± 0.6 | 2.7 ± 0.6 | 2.7 ± 0.7 | 8.6 ± 2.4 |
| 3 | 0.39 ± 0.06 | 31.3 ± 5.5 | >100 | 34 ± 11 | >100 |
| 4 | 0.67 ± 0.06 | 3.0 ± 0.8 | 4.3 ± 0.7 | 3.6 ± 0.4 | 5.7 ± 2.5 |
| 5 | 0.41 ± 0.05 | 2.7 ± 0.6 | 4.0 ± 0.3 | 2.7 ± 0.3 | 4.7 ± 0.6 |
| 6 | 0.79 ± 0.10 | 36.3 ± 6.1 | >50 | 4.9 ± 1.2 | >50 |
| 7 | 0.35 ± 0.08 | 3.3 ± 0.1 | 4.5 ± 0.4 | 2.9 ± 0.4 | 7.1 ± 4.2 |

2.3 Determination of Cytotoxicity to Mammalian Cells ($IC_{50}$)

Cytotoxicity tests of the invented compounds against African green monkey kidney fibroblast (Vero cells), Human epidermoid carcinoma (KB) cells, Human breast cancer (BC) cells were performed according to the protocol described by Skehan et al (1990).

These compounds have selectivity against malaria parasites with no or less effect on mammalian cell lines. The cytotoxicity to three mammalian cell lines (Vero, KB, and BC cells) is as summarized in Table 3.

TABLE 3

Cytotoxicity of the 2,4-diaminopyrimidine derivative compounds to mammalian cells ($IC_{50}$)

| Example | $IC_{50}$ (µM) | | |
|---|---|---|---|
| | Vero Cells | KB cells | BC Cells |
| Pyr | 32 | 109 | 40.0 |
| 1 | 55 | 113 | 268.0 |
| 2 | >50 | 150 | 250.0 |
| 3 | 20 | 71 | 500.0 |
| 4 | 2.1 | 1.6 | 1.6 |
| 5 | 3 | 15 | 3.0 |
| 6 | 20 | 9.3 | 22.8 |
| 7 | 15 | 6.4 | 4.9 |

2.4 Determination of Antibacterial Activities ($IC_{50}$)

Antibacterial activity of the invented compounds was determined by incubation of suspension of bacteria, *Staphylococcus aureus* and *E. coli* with a serial dilution of the drugs for 20 hours in a 96-well plate. Bacterial growth inhibition was determined by spectrophotometer at 600 nm. The $IC_{50}$-values was determined from the sigmoidal curve obtained by plotting the percentages of bacterial growth against drug concentrations.

These compounds have selectivity against malaria parasites with no or less effect on bacteria. The antibacterial activities to *S. aureus*, and *E. coli* are as summerized in Table 4.

TABLE 4

Antibacterial activities ($IC_{50}$) of 2,4-diaminopyrimidine derivative compounds

| Example | $IC_{50}$ (µM) | |
|---|---|---|
| | *S. aureus* | *E. coli* |
| Trimethoprim | 6.0 | 2.3 |
| 1 | >10 | >10 |
| 2 | >50 | >50 |
| 3 | >50 | >50 |
| 4 | >50 | >50 |
| 5 | 38.0 | >50 |
| 6 | >50 | >50 |
| 7 | >50 | >50 |

REFERENCES

1. Hitchings, G. H., Russell, P. B., Falco, E. A. U.S. Pat. No. 2,576,939 (1951)
2. Hitchings, G. H., Russell, P. B., Falco, E. A. U.S. Pat. No. 2,594,309 (1952)
3. Hitchings, G. H., Russell, P. B., Falco, E. A. U.S. Pat. No. 2,602,794 (1952)
4. Hitchings, G. H., Russell, P. B. U.S. Pat. No. 2,624,731 (1953)
5. Jacob, R. M. U.S. Pat. No. 2,680,740 (1954)
6. Hitchings, G. H., Russell, P. B., Falco, E. A. U.S. Pat. No. 2,688,019 (1954)
7. Mentha, J. W., Shaffner, J. V., Cresswell, R. M. U.S. Pat. No. 3,849,416 (1974)
8. Mentha, J. W., Shaffner, J. V., Cresswell, R. M. U.S. Pat. No. 3,939,181 (1976)
9. Greenspan, G., Ress, R. W., Russell, P. B. U.S. Pat. No. 3,940,393 (1976)
10. Stevens, M. F. G., Griffin, R. J., Meek, M. A. U.S. Patent No. 4,992,444 (1991)
11. Russell, P. B., Hitchings, G. H. 2,4-Diaminopyrimidines as Antimalarials. III. 5-Aryl Derivatives. *J. Am. Chem. Soc.* 73: 3763-3770 (1951)
12. Chase, B. H., Walker, J. The Preparation of Enol Ethers from Certain β-Keto-nitriles. *J. Chem. Soc.* 3518-3525 (1953)
13. Blaney, J. M., Hansch, C., Silipo, C., Vittoria, A. Structure-Activity Relationships of Dihydrofolate Reductase Inhibitors. *Chem. Rev.* 84: 333-407 (1984)
14. McKie, J. H., Douglas, K. T., Chan, C., Roser, S. A., Yates, R., Read, M., Hyde, J. E., Dascombe, M. J., Yuthavong, Y., Sirawaraporn, W. Rational Drug Design Approach for Overcoming Drug Resistance: Application to Pyrimethamine resistance in Marlaria. *J. Med. Chem.* 41: 1367-1370 (1998)
15. Barlin, G. B., Kotecka, B., Rieckmann, K. H. Potential Antimalarials. XXII. Some 2,4-Diamino-5-(3- and 4-trifluoromethylphenyl and 3,4-methylenedioxyphenyl) pyrimidines. *Aust. J. Chem.* 49: 647-650 (1996)
16. Tarnchompoo, B., Sirichaiwat, C., Phupong, W., Intaraudom, C., Sirawaraporn, W., Kamchonwongpaisan, S., Vanichtanankul, J., Thebtaranonth, Y., Yuthavong, Y. Development of 2,4-Diaminopyrimidines as Antimalarials Based on Inhibition of the S108N and C59R+S108N Mutants of Dihydrofolate Reductase from Pyrimethamine-Resistant *Plasmodium falciparum*. *J. Med. Chem.* 45: 1244-1252 (2002)

17. Trager, W., Jensen, J. B. Human Malaria Parasites in Continuous Culture. *Science*: 193: 673-675 (1976)
18. Desjardins, R. E., Canfield, C. J., Haynes, J. D., Chulay, J. D. Quantitative Assessment of Antimalarial Activity in vitro by a Semiautomated Microdilution Techniques. *Antimicrob. Agents Chemother*. 16: 710-718 (1979)
19. Skehan, P., Storeng, R., Scudiero, D., Monks, A., McMahon, J.; Vistica, D., Warren, J. T., Bokesch, H., Kenney, S., Boyd, M. R. New Colorimetric Cytotoxicity Assay for Anticancer-Drug Screening. *J. Natl. Cancer Inst*. 82: 1107-1112 (1990)

We claim:

1. A method for inhibiting a mutant dihydrofolate reductase (DHFR) protein in drug-resistant malaria, comprising administering a pharmaceutical composition which comprises a compound of formula:

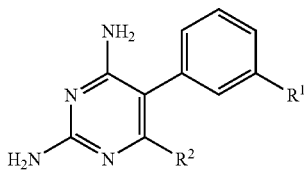

wherein $R^1$ is a hydrogen or halogen atom, and $R^2$ is selected from the group consisting of: $C_5$ to $C_6$ alkyl; $C_1$ to $C_3$ alkyl having a terminal aromatic substituent or an alkoxycarbonyl substituent; and an aryloxyalkoxyalkyl group, wherein said malaria is caused by *Plasmodium falciparum* comprising the mutant DHFR protein with at least three mutations, wherein the mutations are selected from the group consisting of N51I, C59R, S108N, and I164L.

2. The method of claim 1, wherein the *Plasmodium falciparum* is resistant to antifolate compounds.

3. The method of claim 2, wherein the *Plasmodium falciparum* is resistant to pyrimethamine.

4. The method of claim 1, wherein said *Plasmodium falciparum* DHFR protein comprises at least four mutations.

5. The method of claim 1, wherein said at least three mutations comprise C59R, S108N, and I164L.

6. The method of claim 1, wherein said at least three mutations comprise N51I, C59R, and S108N.

7. The method of claim 4, wherein said at least four mutations comprise N51I, C59R, S108N, and I164L.

8. The method of claim 1, wherein $R^2$ is 3-phenylpropyl, 3-(4-methoxyphenyl)propyl, 3-methoxycarbonylpropyl or 2-(3-phenoxypropyloxy)ethyl.

9. The method of claim 1, wherein $R^1$ is chloro.

10. The method of claim 1, wherein the compound is 2,4-diamino-5-(3-chlorophenyl)-6-(3-phenylpropyl)pyrimidine, 2,4-diamino-5-(3-chlorophenyl)-6-[3-(4-methoxyphenyl)propyl]pyrimidine, 2,4-diamino-5-(3-chlorophenyl)-6-(3-methoxycarbonylpropyl)pyrimidine, or 2,4-diamino-5-(3-chlorophenyl)-6-[2-(3-phenoxypropyloxy)ethyl] pyrimidine.

11. The method of claim 1, wherein $R^2$ is n-hexyl, 3-phenylpropyl, or 3-methoxycarbonylpropyl.

12. The method of claim 1, wherein $R^1$ is hydrogen.

13. The method of claim 12, wherein the compound is 2,4-diamino-5-phenyl-6-(n-hexyl)pyrimidine, 2,4-diamino-5-phenyl-6-(3-phenylpropyl)pyrimidine, or 2,4-diamino-5-phenyl-6-(3-methoxycarbonylpropyl)pyrimidine.

14. A method for inhibiting a mutant dihydrofolate reductase (DHFR) protein in drug-resistant malaria, comprising administering a pharmaceutical composition which comprises a compound of formula:

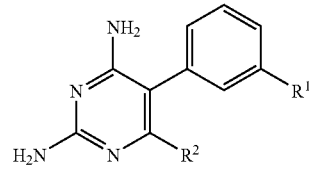

wherein $R^1$ is a hydrogen or halogen atom, and $R^2$ is selected from the group consisting of: $C_5$ to $C_6$ alkyl; $C_1$ to $C_3$ alkyl having a terminal aromatic substituent or an alkoxycarbonyl substituent; and an aryloxyalkoxyalkyl group, wherein said malaria is caused by *Plasmodium falciparum* comprising the mutant DHFR protein with at least four mutations selected from the group consisting of N51I, C59R, S108N, and I164L.

* * * * *